United States Patent [19]

Naik et al.

[11] Patent Number: 4,731,378

[45] Date of Patent: Mar. 15, 1988

[54] PESTICIDAL FORMULATIONS

[75] Inventors: Arundev H. Naik, Leverkusen; Hans U. Sieveking, Cologne; Wilhelm Stendel, Wuppertal; Herbert Voege, Leverkusen, all of Fed. Rep. of Germany

[73] Assignee: Bayer Aktiengesellschaft, Leverkusen, Fed. Rep. of Germany

[21] Appl. No.: 670,703

[22] Filed: Nov. 13, 1984

Related U.S. Application Data

[63] Continuation of Ser. No. 470,024, Feb. 25, 1983, abandoned.

[30] Foreign Application Priority Data

Mar. 9, 1982 [DE] Fed. Rep. of Germany ....... 3208333

[51] Int. Cl.$^4$ .................... A61K 31/215; A01N 53/00
[52] U.S. Cl. .................................................. 514/531
[58] Field of Search ......................................... 514/531

[56] References Cited

U.S. PATENT DOCUMENTS 4,107,302 8/1978 Watanabe .
4,325,969 4/1982 Brown .
4,341,760 7/1982 Matthewson .

*Primary Examiner*—Sam Rosen
*Attorney, Agent, or Firm*—Sprung Horn Kramer & Woods

[57] ABSTRACT

The invention relates to pesticidal formulations and their use, said pesticidal formulations consisting essentially of at least one pesticidal active pyrethroid compound and containing at least one surface active agent, water and, optionally, up to 40 parts by weight of a water-miscible solvent and up to 10 parts by weight of auxiliaries.

7 Claims, No Drawings

PESTICIDAL FORMULATIONS

This is a continuation of application Ser. No. 470,024, filed Feb. 25, 1983, now abandoned.

The invention relates to pesticidal formulations consisting of at least one pesticidal active compound, at least one surface-active agent, if appropriate a water-miscible solvent, water and if appropriate auxiliaries, to their preparation and to their use in combating harmful and troublesome pests.

Spray treatments and dip treatments of animals or objects have already been disclosed, in which the animals or objects are treated with a pesticidal active compound in a mixture of solvents, emulsifiers, wetting agents and other auxiliaries. These formulations are present as so-called emulsion concentrates, and, before use are diluted with water to the desired use concentration, that is to say before application by spraying or dipping takes place. The conventional emulsion concentrates for use in dipping baths or as spray formulations are prepared by dissolving the active compound in a suitable hydrophobic solvent or solvent mixture and by adding suitable emulsifiers. When diluted with water, for use, oil-in-water emulsions are formed, the stability of which can be adversely affected in very different ways, and the effectiveness of which can be adversely affected by the following factors: time, temperature, dissolved salts, specific gravity of the emulsion concentrate (phase separation), contamination of the dipping baths (adsorption of the emulsion concentrate onto dirt particles and consequent accelerated sedimentation); selective adsorption of the active compound onto the animal hair and consequent accelerated exhaustion of the dipping baths; and water evaporation and solvent evaporation in the dipping baths, which cause changes in concentration.

Solvent-free or diluent-free formulations were reported in U.S. Pat. specification No. 4,195,083. In these formulations, the solvent has been very substantially replaced by liquid pesticides. However, the emulsions obtained on dilution do not differ from emulsions which contain conventional hydrophobic solvents. The milky appearance of such emulsions indicates the presence of relatively large particle diameters, which are thermodynamically unstable and therefore unable to eliminate the negative effect of the contamination in the dipping baths.

The invention relates to pesticidal formulations consisting of 0.5 to 50 parts by weight of a pesticidal active compound, 5 to 80 parts by weight of a surface-active agent, 5 to 90 parts by weight of water and, if appropriate, up to 40 parts by weight of a water-miscible solvent, and up to 10 parts by weight of auxiliaries.

Preferably, the pesticidal formulations according to the invention consist of 1 to 30 parts by weight of a pesticidal active compound, 10 to 50 parts by weight of a surface-active agent, 40 to 90 parts by weight of water and, if appropriate, up to 20 parts by weight of a water-miscible solvent and up to 5 parts by weight of auxiliaries.

Those pesticidal formulations which contain a non-ionic, water-soluble, surface-active agent having an HLB value (hydrophilic/lipophilic/balance) greater than 10 are particularly suitable for combating harmful and troublesome pests.

The pesticidal formulations according to the invention can contain auxiliaries, such as preservatives, antioxidants, stabilisers, dyestuffs, antifoaming agents, adhesives and synergists, and are employed for spray treatment and dip treatment of animals and objects. The formulations according to the invention are particularly suitable for use in dipping baths with capacities of up to 30,000 l.

Suitable active compounds are hydrophilic or lipophilic pesticides.

The following active compounds are particularly suitable for the pesticidal formulations according to the invention:

($\alpha$-cyano-4-fluoro-3-phenoxy)-benzyl 3-[2-(4-(chlorophenyl)-2-chlorovinyl]-2,2-dimethylcyclopropanecarboxylate (flumethrin);

$\alpha$-cyano-3-phenoxybenzyl 2,2-dimethyl-3-(2,2-dichlorovinyl)-cyclopropanecarboxylate;

$\alpha$-cyano-3-phenoxybenzyl $\alpha$-(p-Cl-phenyl)-isovalerate;

cyano-(3-phenoxyphenyl)-methyl 3,3-dimethyl-spiro-[cyclopropan-1,1-(1H)-indene]-2-carboxylate;

3-methyl-2-[2,4-dimethyl-phenylimino]-thiazoline;

2-(4-chloro-2-methylphenylimino)-3-methylthiazolidine;

2-(4-chloro-2-methylphenylimino)-3-(isobut-1-enyl)-thiazolidine;

diethoxy-thiophosphoryloxyiminophenylacetonitrile;

diphenylcarbodiimides, as described in DE-OS [German Published Specification] No. 2,532,259;

O-ethyl O-(quinol-8-yl)benzenethiophosphonate;

2-isopropoxy-phenyl N-methylcarbamate; naphth-1-yl N-methylcarbamate;

O,O-diethyl O-4-bromo-2,5-dichlorophenyl thiophosphate;

2,3-p-dioxaneditiol-S,S-bis-(O,O-diethylphosphorodithionate);

2-chloro-1-(2,4-dichlorophenyl)-vinyl diethyl phosphate;

O,O-diethyl S-(p-chlorophenylthio)-methyl phosphorodithioate;

O,O-dimethyl O-(3-methyl-4-methylthiophenyl)thionophosphate;

O,O-diethyl O-2-iospropyl-4-methyl-6-pyrimidyl phosphorothioate; and

O,O,O',O'-tetraethyl S,S-methylene-di-(phosphorodithioate).

Preferred surface-active agents according to the invention are non-ionic, water-soluble emulsifiers having an HLB (hydrophilic/lipophilic balance) greater than 10. For example: Emulvin W ® (Bayer AG), alkylaryl polyglycol ether; Emulgator NP 10 ® (Bayer AG), alkylaryl polyglycol ether; Renex 678 ® (Atlas Chemical Industries), polyoxyethylene alkylaryl ether; Tween 40 ® (Atlas), polyoxyethylene sorbitan monopalmitate; Myrj 53 ® (Atlas), polyoxyethylene stearate; Atlas G 3707 ®, polyoxyethylene lauryl ether; Atlas G 3920 ®, polyoxyethylene oleyl ether; Atlas G 9046 T ®, polyoxyethylene mannitan monolaurate; Emulgator 1371 A ® (Bayer AG), alkylaryl sulphonate; Emulgator 1371 B ® (Bayer AG), alkyl polyglycol ether; Emulgator 1736 ® (Bayer AG), alkyl polyglycol ether (oleyl polyglycol ether); Emulgator OX ® (Bayer AG), alkyl polyglycol ether (dodecyl polyglycol ether); Ninox BM-2 ® (Stepan Chemical Co.), ethoxylated nonylphenol; Triton X-100 ® (Rohm & Haas Co.), isoo tylphenolpolyethoxyethanol; Cremophor EL ®.

The water-miscible solvents mentioned below are preferably used for the preparation of the pesticidal formulations according to the invention:

methanol, ethanol, propanol, preferably isopropanol, dimethylsulphoxide, dimethylformamide, glycerol, ethylene glycol monomethyl ether (methyl-Cellosolv), ethylene glycol monomethyl ether acetate (methyl-Cellosolv acetate), ethylene glycol monoethyl ether, diethylene glycol, diethylene glycol monomethyl ether (methoxyethoxyethanol, methyl Carbitol), diethylene glycol monoethyl ether, (ethyldiglycol, Carbitol), diethylene glycol monoethyl ether acetate, diethylene glycol dimethyl ether, diethylene glycol diethyl ether (diethyl-Carbitol), polyethylene glycols, propylene glycols, polypropylene glycols and ketones, such as acetone and methyl ethyl ketone.

FORMULATIONS

The formulations according to the invention are prepared by dissolving the active compound in an emulsifier or in an emulsifier/solvent mixture, while warming if necessary, and by adding the required amount of water, and while stirring with a normal static mixer. A special homogenising apparatus is not required.

The examples which follow of new formulations are intended to illustrate these, but not to restrict the invention.

EXAMPLE 1

| Active compound: | (α-cyano-4-fluoro-3-phenoxy)-benzyl 3-[-2-(4-chlorophenyl)-chloro-vinyl]-2,2-dimethyl-cyclopropanecarboxylate | 5 g |
| --- | --- | --- |
| Emulsifier: | Emulvin W ® (alkylaryl polyglycol ether) | 30 g |
| Water | to make up to | 100 ml |

EXAMPLE 2

| Active compound: | as in Example 1 | 0.5 g |
| --- | --- | --- |
| Emulsifier: | Renex 678 ® (polyoxyethylene alkylaryl ether) | 8.0 g |
| Water: | to make up to | 100 m |

EXAMPLE 3

| Active compound: | as in Example 1 | 2 g |
| --- | --- | --- |
| Emulsifier: | NP 10 ® (alkylaryl polyglycol ether) | 40 g |
| Water: | to make up to | 100 ml |

EXAMPLE 4

| Active compound: | 3-methyl-2-[2,4-dimethyl-phenylimino]-thiazoline | 15 g |
| --- | --- | --- |
| Emulsifier: | Renex 678 ® (polyoxyethylene alkylaryl ether) | 40 g |
| Water: | to make up to | 100 ml |

EXAMPLE 5

| Active compound: | 2-(4-chloro-2-methylphenyl-imino)-3-(isobut-1-enyl)-thiazolidine | 20 g |
| --- | --- | --- |
| Solvent: | ethanol | 30 g |
| Emulsifier: | Cremophor-EL ® | 45 g |
| Water: | to make up to | 100 ml |

EXAMPLE 6

| Active compound: | O,O—diethyl O-4-bromo-2,5-dichloro-phenyl thiophosphonate | 20 g |
| --- | --- | --- |
| Emulsifier: | Triton X-100 ® (isooctyl-phenol polyethoxyethanol) | 30 g |
| Water: | to make up to | 100 ml |

EXAMPLE 7

| Active compound: | 2-isopropoxy-phenyl N—methyl-carbamate | 10 g |
| --- | --- | --- |
| Emulsifier: | Atlas G 3920 ® (polyoxyethylene oleyl ether) | 50 g |
| Solvent: | isopropanol | 20 g |
| Water: | to make up to | 100 ml |

EXAMPLE 8

| Active compound: | pentafluorophenyl-methyl 3(2,2-dichloroethenyl)-2,2-dimethyl-cyclopropane-carboxylate | 4 g |
| --- | --- | --- |
| Emulsifier: | Emulvin W ® (alkylaryl polyglycol ether) | 28 g |
| Water: | to make up to | 100 ml |

EXAMPLE 9

| Active compound: | O—ethyl O—(quinol-8-yl) benzenethiophosphonate | 10 g |
| --- | --- | --- |
| Solvent: | diethylene glycol monomethyl ether | 7 g |
| Emulsifier: | SZZ 1166 B ® (alkylaryl polyglycol ether) | 25 g |
| Water: | to make up to | 100 ml |

The following examples on improved activity are intended to illustrate the superiority of the novel formulations.

(A) In testing the formulations according to the invention in respect of their activity, it was found, surprisingly, that these formulations are not only equally good but even have a better activity than conventional emulsion concentrates containing organic solvents. This is shown by the following experiment:

For comparison, ticks of the *Boophilus microplus* species (Biarra strain) were treated, in a dipping test, with the active compound flumethrin in a conventional formulation and a formulation according to the invention. After 8 minutes, 50% of the ticks were washed off with tap water, and 50% were not. The $LC_{100}$ (lethal concentration 100%) values can be seen from the table below:

| New formulation | $LC_{100}$ |
| --- | --- |
| according to Example 1 | 1 ppm in the case of ticks not washed subsequently |
| | 4 ppm in the case of ticks washed subsequently. |
| Conventional formulation | 2 ppm in the case of ticks |
| 7.5% strength emulsion | not washed subsequently 64 ppm |

| concentrate containing an aromatic solvent | in the case of ticks washed subsequently. |

(B) In a second experiment, cattle infested with the same ticks were each sprayed with 10 liters of liquid which contained 2.5 mg of flumethrin as the active compound.

When the new formulation according to Example 1 was employed for the preparation of the use concentration, the activity was 92%.

In contrast, a corresponding emulsion prepared from a conventional emulsion concentrate had an activity of only 61%.

What is claimed is:

1. A pesticidal consisting essentially of 0.5 to 50 parts by weight of at least one pesticidal active pyrethroid compound selected from the group consisting of [α-cyano-4-fluoro-3-phenoxy)-benzyl 3-[2-(4-chlorophenyl)-2-chlorovinyl]-2,2-dimethylcyclopropanecarboxylate (flumethrin) and (α-cyano-3-phenoxybenzyl 2,2-dimethyl-3-(2,2-dichlorovinyl)-cyclopropanecarboxylate, 5 to 80 parts by weight of at least one surface active agent selected from the group consisting of alkylaryl polyglycol ether, polyoxyethylene alkylaryl ether, polyoxyethyelene sorbitan monopalmitate, polyoxyethylene stearate, polyoxyethylene lauryl ether, polyoxyethylene oleyl ether, polyoxyethylene mannitan monolaurate and alkyl polyglycol ether, 5 to 90 parts by weight of water and optionally up to 40 parts by weight of a water-miscible solvent and up to 10 parts by weight of auxiliaries.

2. A method of combatting pests of warm-blooded animals which comprises applying to said animals a pesticide formulation of claim 1.

3. A method of claim 2 wherein the pests are ectoparasites.

4. A method of combatting pests and parasites of warm-blooded animals which comprises spraying said animals with a formulation of claim 1.

5. A pesticidal formulation according to claim 1 wherein the pesticidal active pyrethroid compound is (α-cyano-3-phenoxybenzyl 2,2-dimethyl-3-(2,2-dichlorovinyl)-cyclopropanecarboxylate.

6. A pesticidal formulations of claim 1 wherein the alkyl polyglycol ether is a member selected from the group consisting of oleyl polyglycol ether, dodecyl polyglycol ether, ethoxylated nonylphenol and isoctylphenolpolyethoxyethanol.

7. A pesticidal formulation consisting essentially of 0.5 to 50 parts by weight of at least one pesticidal active pyrethroid compound, said pesticidally active compound being α-cyano-4-fluoro-3-phenoxy)-benzyl 3-[2-(4-chlorophenyl)-chloro-vinyl]-2,2-dimethylcyclopropanecarboxylate, 5 to 80 parts by weight of at least one surface active agent selected from the group consisting of alkylaryl polyglycol ether, polyoxyethylene alkylaryl ether, polyoxyethylene sorbitan monopalmitate, polyoxyethylene stearate, polyoxyethylene lauryl ether, polyoxyethylene oleyl ether, polyoxyethylene mannitan monolaurate, alkyl polyglycol ether, 5 to 90 parts by weight of water and optionally up to 40 parts by weight of a water-miscible solvent and up to 10 parts by weight of auxiliaries.

* * * * *